(12) United States Patent
Dreyfuss

(10) Patent No.: US 7,695,495 B2
(45) Date of Patent: *Apr. 13, 2010

(54) PEEK THREADED SUTURE ANCHOR

(75) Inventor: Peter J. Dreyfuss, Naples, FL (US)

(73) Assignee: Arthrex, Inc., Naples, FL (US)

(*) Notice: Subject to any disclaimer, the term of this patent is extended or adjusted under 35 U.S.C. 154(b) by 0 days.

This patent is subject to a terminal disclaimer.

(21) Appl. No.: 11/299,664

(22) Filed: Dec. 13, 2005

(65) Prior Publication Data

US 2007/0135841 A1 Jun. 14, 2007

(51) Int. Cl.
*A61B 17/04* (2006.01)
*A61B 17/06* (2006.01)
*A61F 2/28* (2006.01)

(52) U.S. Cl. .................. 606/232; 606/301; 606/224

(58) Field of Classification Search .............. 606/72, 606/73, 222–227, 232, 301
See application file for complete search history.

(56) References Cited

U.S. PATENT DOCUMENTS

| 4,632,100 | A | 12/1986 | Somers et al. |
| 5,037,422 | A | 8/1991 | Hayhurst et al. |
| 5,046,513 | A | 9/1991 | Gatturna et al. |
| 5,141,520 | A | 8/1992 | Goble et al. |
| 5,156,616 | A | 10/1992 | Meadows et al. |
| 5,370,662 | A | 12/1994 | Stone et al. |
| 5,417,712 | A * | 5/1995 | Whittaker et al. ............ 606/232 |
| 5,964,783 | A | 10/1999 | Grafton et al. |
| 6,652,563 | B2 * | 11/2003 | Dreyfuss .................... 606/232 |
| 6,840,953 | B2 * | 1/2005 | Martinek .................... 606/232 |
| 2004/0138707 | A1 | 7/2004 | Greenhalgh |

FOREIGN PATENT DOCUMENTS

| EP | 0 663 184 | 7/1995 |
| EP | 1 584 296 | 10/2005 |

OTHER PUBLICATIONS

European Search Report, EP 06 12 5921, Mar. 28, 2007.

* cited by examiner

*Primary Examiner*—(Jackie) Tan-Uyen T. Ho
*Assistant Examiner*—Melissa Ryckman
(74) *Attorney, Agent, or Firm*—Dickstein Shapiro LLP

(57) ABSTRACT

A threaded suture anchor formed of a material comprising polyether-ether ketone (PEEK) has a suture loop that is disposed internally within the suture anchor. The suture loop can extend through a substantial length of the anchor body with the ends of the suture loop secured at the distal end of the anchor and the proximal end of the loop being flush with or recessed just below the proximal surface of the proximal end of the anchor. The anchor body can be threaded and have a tapered distal portion.

10 Claims, 3 Drawing Sheets

PEEK THREADED SUTURE ANCHOR

FIELD OF THE INVENTION

The present invention relates to an apparatus for anchoring surgical suture to bone. More specifically, the present invention relates to a threaded suture anchor formed of polyether-ether ketone (PEEK) having an internal suture loop for receiving one or more strands of suture to anchor the suture to bone during arthroscopic surgery.

BACKGROUND OF THE INVENTION

When soft tissue tears away from bone, reattachment becomes necessary. Various devices, including sutures alone, screws, staples, wedges, and plugs have been used in the prior art to secure soft tissue to bone.

Recently, various types of threaded suture anchors have been developed for this purpose. Some threaded suture anchors are designed to be inserted into a pre-drilled hole. Other suture anchors are self-tapping.

U.S. Pat. No. 4,632,100 discloses a cylindrical threaded suture anchor. The suture anchor of the '100 patent includes a drill bit at a leading end for boring a hole in a bone, followed by a flight of threads spaced from the drill bit for securing the anchor into the hole created by the drill bit.

U.S. Pat. No. 5,370,662 discloses a suture anchor having threads which extend to the tip of the anchor. U.S. Pat. No. 5,156,616 discloses a similar suture anchor having an axial opening for holding a knotted piece of suture.

All of the above-noted suture anchors include structure for attaching the suture to the anchor. U.S. Pat. No. 4,632,100, for example, discloses a press-fitted disc and knot structure which secures the suture to the anchor. In other suture anchors, such as those disclosed in U.S. Pat. No. 5,370,662, the suture is passed through an eyelet located on the proximal end of the anchor. In the case of a bioabsorbable suture anchor, the suture may be insert molded into the anchor, as disclosed in U.S. Pat. No. 5,964,783. However, the materials used to make such suture anchors can impose limitations on their use. For example, suture anchors made of metal or certain polymers are not radiolucent or radioopaque and thus are not visible on magnetic resonance imaging ("MRI") scans. In addition, such suture anchors may not be revisable once implanted in the bone.

Problems can also arise if the structure for attaching the suture fails, allowing the suture to become detached from the anchor. Also, the suture often is exposed to abrasion or cutting by sharp or rough areas along the walls of the bone canal into which the anchor is inserted.

Moreover, the eyelet or, in the case of U.S. Pat. No. 4,632,100, the axial opening for receiving the disc to which the suture is knotted, is formed as part of the drive head of the known suture anchors. Combining these two functions in one structure often tends to weaken the drive head.

In addition, various other modifications to the drive head often are employed in connection with suture attachment. For example, recessed grooves may be formed on opposite sides of the drive head to receive and protect the suture from abrasive areas of the suture anchor tunnel or to facilitate mating between the anchor to the driver. In such cases, the drive head often must be made of a larger diameter to recover the mechanical strength lost from the removal of material relating to the suture-attachment or suture-protection modifications.

Further, the prior art suture anchors having eyelets extending from the proximal ends require countersinking of the eyelet below the bone surface to avoid having the patient's tissue abrade against the exposed eyelet. As a result, suture attached to the eyelet is vulnerable to abrasion by the bony rim of the countersunk hole into which the suture anchor is installed. In addition, in biodegradable suture anchors, the suture eyelet can degrade rapidly, causing the suture to become detached from the anchor prematurely.

Accordingly, there is a need for a threaded suture anchor to which suture is secured effectively so as to prevent detachment of the suture. It is further desirable for such suture anchors to have eyelets that will not abrade tissue and which do not require countersinking. In addition, a need exists for a suture anchor or implant formed by a material which is visible on MRI scans and is revisable following implantation.

BRIEF SUMMARY OF THE INVENTION

The suture anchor of the present invention overcomes the disadvantages of the prior art discussed above by providing a threaded suture anchor having a suture loop disposed inside the body of the suture anchor. In one embodiment, the suture anchor is formed from a material comprising polyether-etherketone ("PEEK"). The advantages of PEEK are described in a white paper entitled, "New Materials in Sports Medicine," Arthrex, Inc. 2005, the disclosure of which is herein incorporated by reference.

The proximal end surface of the threaded suture anchor of the present invention is preferably smooth and rounded to minimize suture abrasion, while the distal portion of the anchor is tapered to an elongated point to enable the anchor to be self-tapping. The proximal end portion of the suture anchor body has a hexagonally shaped opening to accept a hexagonal drive head.

The internal suture loop extends through a substantial length of the anchor body with the ends of the suture loop secured onto the distal end portion of the anchor and the proximal end of the loop being flush with or recessed just below the plane across the proximal face of the anchor.

Advantageously, suture attached to the anchor through the suture loop exits the suture anchor through a central bore in the anchor, which prevents suture abrasion by the wall of the bone tunnel into which the anchor is inserted.

Other features and advantages of the present invention will become apparent from the following description of the invention, which refers to the accompanying drawings.

DETAILED DESCRIPTION OF THE INVENTION

Figure 1:
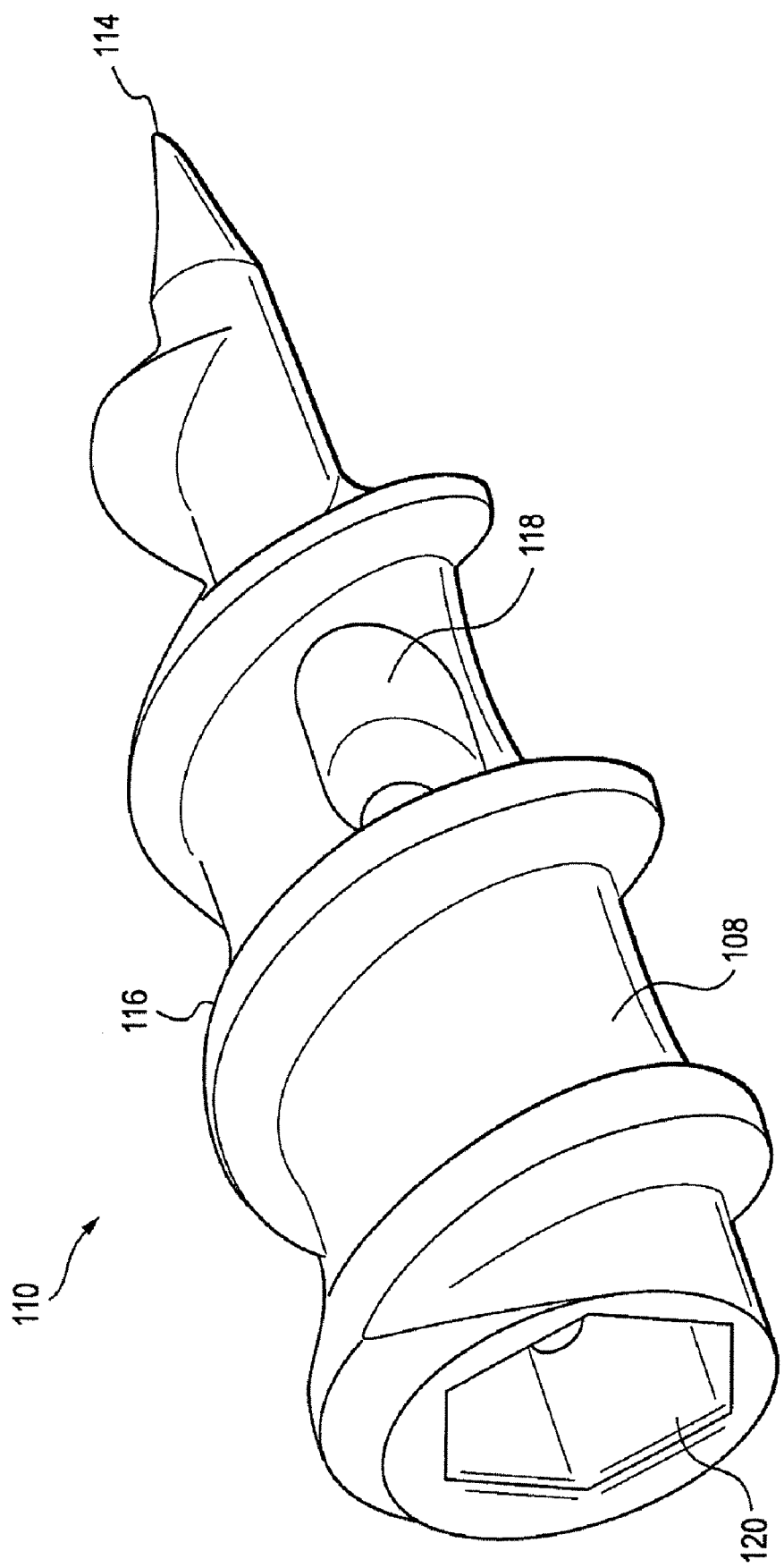
FIG. 1 is a perspective view of a first preferred embodiment of a suture anchor according to the present invention.
Figure 2:
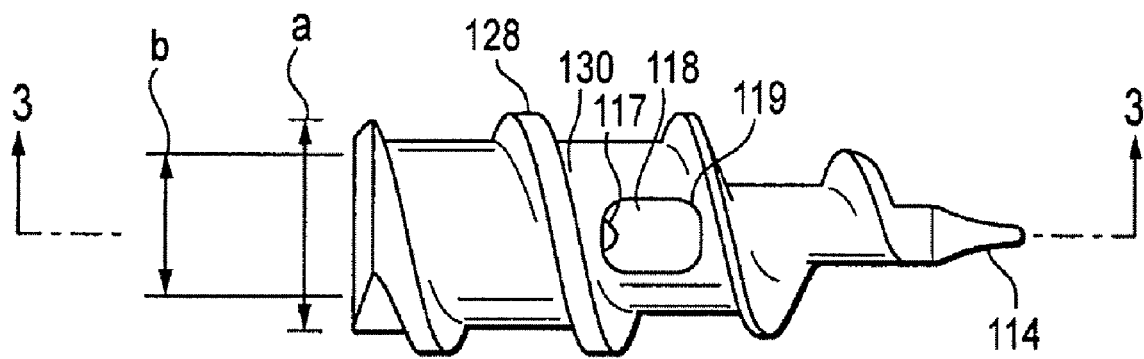
FIG. 2 is a side elevational view of the suture anchor shown in FIG. 1.

FIGS. 1 and 2 illustrate a suture anchor according to a first preferred embodiment of the present invention, indicated generally by reference numeral 110. In the preferred embodiment, body 108 of anchor 110 has a length of about 0.55 in., a major diameter "a" of about 0.21 in., and a minor diameter "b" of about 0.14 in. Suture anchor body 108 generally tapers to a narrow point 114 at the distal end thereof. In particular, the major diameter of the anchor body is generally constant along about two-thirds of the length of the body, whereupon the diameter of the anchor then tapers to a relatively sharp point, e.g., approximately 16 degrees. In one embodiment, the relatively sharp distal tip of anchor 110 enables the anchor to be installed without having to first drill a hole in the bone where the anchor 110 is to be installed.

Although such tapering is preferred, suture anchor 110 may be formed to have a less tapered shape, or even cylindrical shape, to accommodate different preferences of the surgeon and/or the application of the suture anchor. For example, the tapered distal end of the anchor may be formed to be more blunt, in which case it is necessary to provide a pre-formed hole in the bone prior to insertion of the suture anchor.

A continuous thread 116 wraps around the body 108 in a clockwise direction, as shown. Anchor 110 has about six flights of thread, with the angle of the proximal surface 128 of each thread being approximately one-third the angle of the distal surface 130 of each thread relative to the horizontal direction perpendicular to the longitudinal axis of the anchor, e.g., 15 degrees versus 45 degrees.

Figure 3:
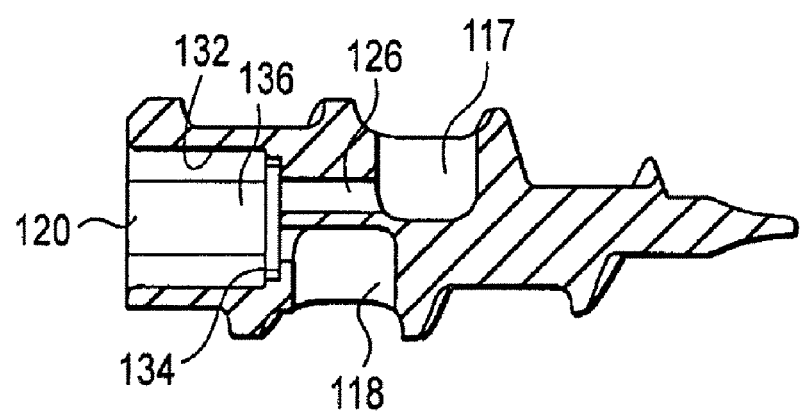
FIG. 3 is a longitudinal sectional view of the suture anchor shown in FIG. 2 through the plane 3-3 indicated therein.

As can be seen more clearly with reference to FIG. 3, the proximal end portion of the anchor has a hexagonally shaped bore 132 having an opening 120 at the proximal end of anchor body 108 and extending into the anchor body approximately one-fourth of the length thereof. Prior art anchors have sharp edges around the drive opening, which is problematic in that sutures passing through the central opening at the proximal end of the anchor can be abraded by the sharp edges, thereby compromising the strength of the sutures. In one embodiment of the suture anchor of the present invention, the peripheral edges defining hexagonally shaped opening 120 is smooth and rounded outwardly with no sharp edges. Preferably, the opening 120 forms a slight lip curving around the diameter of the bore 132. Thus, sutures threaded through the anchor 110, as will be discussed below, will not become frayed upon being pressed or rubbed against the anchor at the proximal opening 120.

A cylindrical bore 136 having a diameter smaller than that of the hexagonally shaped bore 132 extends from the distal end of the hexagonally shaped bore 132 to a position roughly one quarter along the length of anchor body 108. The transition between hexagonally shaped bore 132 and cylindrical bore 136 forms an annular shoulder 134, against which the distal end of a hex driver abuts when inserted into the hexagonally shaped bore 132 to drive the anchor into bone.

Figure 5:
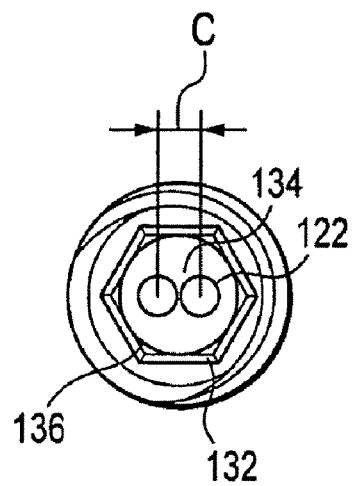
FIG. 5 is a cross sectional view through the suture anchor and suture loop of FIG. 4 through the plane 6-6 indicated therein.

Two longitudinal passageways 126 are formed in anchor body 108 distally to the cylindrical bore 136, extending from the distal end of bore 136 to two corresponding apertures 118 formed opposite to each other in an offset manner through the angled distal portion of suture anchor 110. Referring to the cross-sectional view shown in FIG. 5, the preferred distance "c" between the centers of the two passageways 126 is about 0.55 in.

Apertures 118 each have an inner opening 117 defining the exit from the respective passageway 126, and widen to a larger, exterior opening 119 along the radial surface of anchor body 108. As can be seen in FIG. 2, apertures 118 are disposed between the threads 116 around anchor body 108. Due to the shape of apertures 118 and the angle at which apertures 118 intersect passageways 126, inner openings 117 are slightly oblong and may have an angle along the periphery thereof. Preferably, the peripheral edges defining the inner openings 117 of the suture anchor are smoothed and rounded (e.g., during the manufacturing process) so as to not abrade the suture knots which will be affixed therein (described below).

An eyelet formed of a loop of suture 122 is disposed inside the body of suture anchor 110. The ends of the suture strand forming the loop can be threaded through the longitudinal passageways 126 from the proximal opening 120 and pass into the apertures 118. Threading the ends of the suture through the passageways 126 and the apertures 118 may be facilitated by coating the ends of the suture (having a length longer than the length of the passageways 126) with a stiffening agent.

The proximal-most surface of the suture loop 122 is flush with or slightly recessed from the proximal opening 120, so that the suture loop does not project outside the body 108 of suture anchor 110. Preferably, the suture loop 122 is recessed between 0.05 to 0.14 in. from the plane across the suture anchor 110 at the proximal opening 120 thereof, as measured from the underside of the proximal-most point of the loop 122. The underside position corresponds to the depth into the bore 132 at which a suture strand inserted through the loop 122 would be attached to anchor 110.

Figure 4:
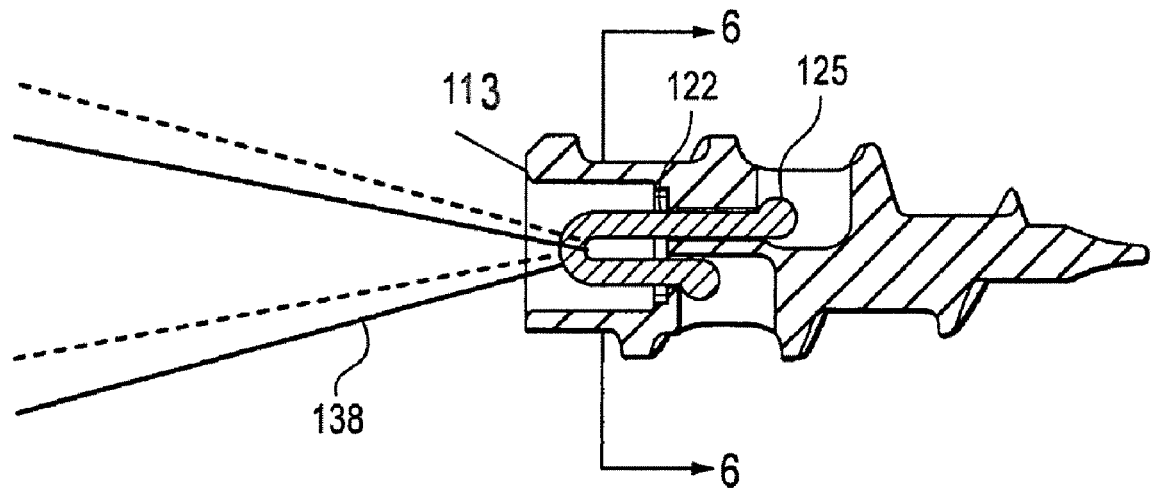
FIG. 4 is a cross sectional view of the suture anchor of FIG. 1 showing the internal suture loop therein, and having suture strands attached to the suture anchor through the internal suture loop.

To secure the suture loop onto anchor body 108, the ends of suture loop 122 are each tied in a knot 125, e.g., an overhand knot, and sealed with a biocompatible adhesive to permanently affix the knot. As illustrated in FIG. 4, knots 125 are then respectively inserted into the apertures 118 so that the knots are substantially entirely fitted within the space of the apertures 118. As shown in FIG. 4, knots 125 are asymmetrically disposed in their respective apertures 118 relative to a most proximal end 113 of the anchor body 108. The smaller diameter of inner openings 117 of apertures 118 prevent the knots 125 from being pulled through into the interior of the anchor 110. Affixed in this manner, suture loop 122 has a pullout strength of 45 lbs. from the suture anchor 110.

Preferably, the suture anchor 110 is formed from a material comprising PEEK. A suture anchor formed from a material comprising PEEK has several advantageous properties. First, PEEK is radiolucent. PEEK does not contain metal and therefore no metallic scatter occurs during magnetic resonance imaging (MRI) scans.

In addition, suture anchors formed by PEEK have significantly reduced notch sensitivity resulting in a more stable and resilient suture anchor. The term "resilient" as used herein is not meant to imply that PEEK material is deformable and recovers its size and shape after deformation, rather is intended to mean that PEEK is capable of withstanding shock and other outside forces without deterioration. Specifically, the term "resilient" is taken from the PEEK-Optima Polymer brochure of Invibio Ltd., UK, 2004, where it is stated that PEEK is "resilient and enduring" in the sense that PEEK is "characterized by its high strength. extreme resistance to hydrolysis and resistance to the effects of ionizing radiation. Therefore, PEEK-OPTIMA can be repeatedly sterilized . . . without significant deterioration of mechanical properties." The construction of an anchor body formed from a material comprising PEEK provides both stable fixation and revisability. Previously available suture anchors may require "wings" or "arms" to provide fixation. In contrast, the threading of the PEEK unibody construction shown in FIGS. 1-5 provide stable fixation without requiring additional structural features. Furthermore, PEEK suture anchors are revisable, for example, by drilling out the anchor.

The mechanical properties of PEEK closely match the mechanical properties of bone: tensile yield strength, shear strength, and modulus. These properties are not significantly degraded by gamma-irradiation, steam-sterilization (water environment), or oxidation (aging). The material is also resistant to heat and requires no special accommodations for shipping and handling.

Preferably, the material forming the suture loop 122 is a #5 USP braided polyester suture or #2 FiberWire™, a high strength suture formed of a braid of polyester and ultrahigh molecular weight polyethylene, coated with silicone, and sold by Arthrex, Inc. of Naples, Fla. However, any suitable coated or uncoated suture material can be used with the suture anchor of the invention.

The suture anchor according to the present invention need not be formed as a threaded device, but can also be formed as a tap-in type anchor. Also, the measurements, angles and ratios between the dimensions of the suture anchor may be varied from those described above so as to be suitable for the conditions and applications in which the suture anchor is to be used.

In manufacturing the suture anchor 110 in accordance with the present invention, the anchor body 108 is machined, with the bores, passageways and apertures described above either being formed during the machining process or formed afterwards. If necessary, the distal tip 114 of the anchor 110 is trimmed to the desired length and the surfaces of the anchor are polished to the desired finish. Alternatively, the anchor body 108 can be cast in a die with the bores, passageways and apertures described above either being formed during the casting process or formed afterwards.

Preferably, the suture anchors according to the present invention are distributed to surgeons with one or more strands of suture 138 already threaded through the suture loop. Such sutures attached to the suture anchor through the internal suture loop must be able to slide smoothly through the slightly recessed loop. Sutures suitable for use in conjunction with the suture anchor and internal suture loop discussed herein include #2 FiberWire™ and #2 braided polyester. If more than one suture strand is provided through the suture loop, each strand is preferably a different color, e.g., green, white, blue, etc., or may be provided with color contrasting strands.

Optionally, or if it becomes necessary due to the pre-threaded suture strands being accidentally removed from the suture loop, the user may be required to thread or re-thread the suture strands through the suture loop. In this case, threading a strand of suture through the suture loop may be facilitated if the ends of the suture strand are coated with a stiffening agent. Alternatively or additionally, a tool may be used to thread the suture strands and/or grasp the end of the suture after passing through the suture loop.

As mentioned above, the suture anchor of the present invention may be installed in the bone without the need to pre-drill a hole in the bone. The suture anchor is installed using a driver having a shaft having a hexagonal cross-section for at least a length equal to the length of the hexagonal bore 132, 232 from proximal opening 120, 220 to the shoulder 134, 234 inside the anchor 110, 210. The driver has a cannula extending through the entire length thereof, with openings at the proximal and distal ends thereof. The outer diameter of the hexagonal shaft can be sized to fit inside the hexagonal bore in the anchor so as to be enabled to drive the same.

With the desired number of suture strands threaded through the suture loop in the suture anchor, the ends of the suture strands are threaded through the cannula in the hex driver from the distal end thereof and exiting from the proximal opening thereof. The distal end of the hexagonal shaft of the driver can be inserted into the proximal end of the anchor while the suture loop is inserted into the distal end opening of the driver. With the distal end of the driver abutting shoulder 134 and the anchor positioned at the location at which it is to be installed, the hex driver is rotated to drive the anchor into the bone until the proximal surface of the anchor is flush with the surface of the bone.

Since it is not necessary for the proximal end of the anchor to be countersunk below the bone surface to prevent tissue abrasion by an exposed suture loop, as is required with prior art devices, the suture anchor of the present invention does not need to be inserted as far as the prior art anchors, while also avoiding abrasion of the sutures by the rim of the bone.

The suture anchor of the present invention provides greater pull-out strength of the suture loop than prior suture anchors. In addition, the suture loop of the present invention, being disposed inside the suture anchor, is protected from abrasion and degradation.

Although the present invention has been described in relation to particular embodiments thereof, many other variations and modifications and other uses will become apparent to those skilled in the art. Therefore, the present invention is to be limited not by the specific disclosure herein, but only by the appended claims.

What is claimed as new and desired to be protected by Letters Patent of the United States is:

1. A suture anchor comprising a threaded anchor body formed of a material comprising polyether-ether ketone, the threaded anchor body having a central bore extending from an opening at a most proximal end of the threaded anchor body through a portion of the length thereof, the anchor body including two channels formed from a distal end of the central bore to two respective apertures formed near the distal end of the threaded anchor body to allow a suture loop to be disposed entirely in the central bore and to have ends of the suture loop affixed in the threaded anchor body, wherein the two apertures are asymmetrically disposed relative to the most proximal end of the anchor body, wherein the ends of the suture loop are affixed to the anchor body at the apertures formed near the distal end thereof by a knot formed at each respective end of the suture loop; and at least one strand of suture threaded through the suture loop and extending out of the proximal end of the suture anchor.

2. The suture anchor according to claim 1, wherein the knots formed at the ends of the suture loop are secured with a biocompatible adhesive.

3. The suture anchor according to claim 1, wherein the anchor body is tapered.

4. The suture anchor according to claim 3, wherein the anchor body is tapered to a substantially narrow point.

5. The suture anchor according to claim 1, wherein the suture loop is slightly recessed from the proximal opening of the anchor body.

6. The suture anchor according to claim 1, wherein the central bore has a cross-sectional shape so as to accommodate a driver head for driving the suture anchor.

7. A suture anchor comprising:
a central anchor body formed of a material comprising polyether-ether ketone, the anchor body having central axis, a proximal end and a distal end;
a drive head disposed on the proximal end of the anchor body;
a continuous thread disposed in a spiral around the central body, the continuous thread extending at least along a major portion of the central anchor body;
two apertures formed on a distal portion of the anchor body, the two apertures being asymmetrically disposed relative to the proximal end of the anchor body; and
a loop of suture disposed completely within the anchor body and having ends passed through the two apertures, wherein the ends of the suture loop are affixed to the anchor body at the two apertures by a knot formed at each respective end of the suture loop; and at least one strand of suture threaded through the suture loop and extending out of the proximal end of the suture anchor.

8. The suture anchor according to claim 7, wherein the central body tapers in a diameter along a major portion thereof from a maximum diameter near the proximal end to a minimum diameter toward the distal end.

9. A suture anchor comprising:

a central anchor body formed of a material comprising polyether-ether ketone, the anchor body having a central axis, a proximal end and a distal end;

a drive head disposed on the proximal end of the anchor body;

a continuous thread disposed in a spiral around the central body, the continuous thread extending at least along a major portion of the central anchor body;

two apertures formed on a distal portion of the anchor body, the two apertures being asymmetrically disposed relative to the proximal end of the anchor body; and a suture strand extending from one of the two apertures to the other of the two apertures in the form of a loop, the loop of suture being disposed completely within the anchor body and having ends passed through the two apertures, wherein the ends of the suture loop are affixed to the anchor body at the two apertures by a knot formed at each respective end of the suture loop; and at least one strand of suture threaded through the suture loop and extending out of the proximal end of the suture anchor.

10. The suture anchor according to claim 9, wherein the central body tapers in a diameter along a major portion thereof from a maximum diameter near the proximal end to a minimum diameter toward the distal end.

* * * * *